(12) United States Patent
Holman et al.

(10) Patent No.: US 7,090,774 B1
(45) Date of Patent: Aug. 15, 2006

(54) METHOD FOR PACKED COLUMN SEPARATIONS AND PURIFICATIONS

(75) Inventors: David A. Holman, Richland, WA (US); Cynthia J. Bruckner-Lea, Richland, WA (US); Fred J. Brockman, Kennewick, WA (US); Darrell P. Chandler, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/177,902

(22) Filed: Oct. 23, 1998

(51) Int. Cl.
   *B01D 15/08* (2006.01)

(52) U.S. Cl. ............... 210/656; 210/657; 210/670; 210/675; 210/691

(58) Field of Classification Search .............. 210/675, 210/691, 289, 291, 635, 656, 657, 670; 251/304; 422/100; 95/82, 89, 90, 113
   See application file for complete search history.

(56) References Cited

U.S. PATENT DOCUMENTS

| | | | | |
|---|---|---|---|---|
| 2,797,150 A | * | 6/1957 | Rigby | .................. 422/100 |
| 3,779,511 A | * | 12/1973 | Wenglar | .................. 251/306 |
| 4,750,707 A | * | 6/1988 | Johncox et al. | .............. 251/304 |
| 4,836,250 A | * | 6/1989 | Krambrock | .................. 137/876 |
| 6,136,197 A | * | 10/2000 | Egorov et al. | .............. 210/656 |

* cited by examiner

Primary Examiner—Ivars C. Cintins
(74) Attorney, Agent, or Firm—Douglas E. McKinley, Jr.

(57) ABSTRACT

The invention encompasses a method of packing and unpacking a column chamber. A mixture of a fluid and a matrix material are introduced through a column chamber inlet so that the matrix material is packed within a column chamber to form a packed column. The column chamber having the column chamber inlet or first port for receiving the mixture further has an outlet port and an actuator port. The outlet port is partially closed for capturing the matrix material and permitting the fluid to flow therepast by rotating relative one to the other of a rod placed in the actuator port. Further rotation relative one to the other of the rod and the column chamber opens the outlet and permits the matrix material and the fluid to flow therethrough thereby unpacking the matrix material from the column chamber.

17 Claims, 7 Drawing Sheets

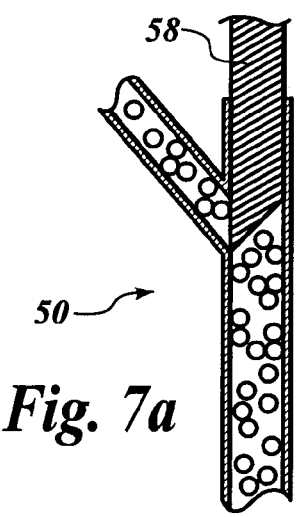
*Fig. 7a*
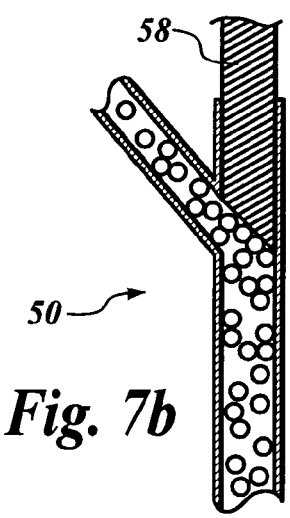
*Fig. 7b*
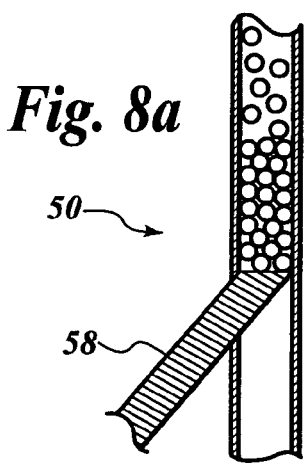
*Fig. 8a*
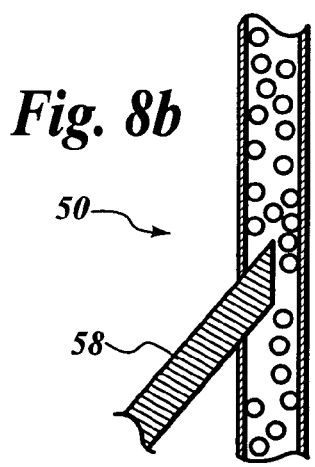
*Fig. 8b*
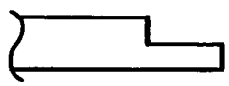   
*Fig. 5d*  *Fig. 5e*  *Fig. 5f*  *Fig. 5g*
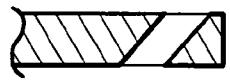 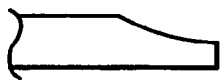 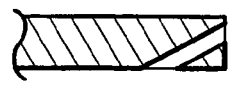
*Fig. 5h*  *Fig. 5j*  *Fig. 5i*
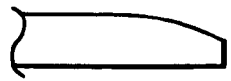 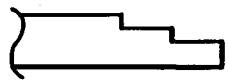
*Fig. 5k*  *Fig. 5l*

METHOD FOR PACKED COLUMN SEPARATIONS AND PURIFICATIONS

This invention was made with government support under Contract DE-AC06-76RLO 1830 awardee by the U.S. Department of Energy. The Government has certain rights in the invention.

TECHNICAL FIELD

The invention pertains to a method and apparatus for column-based separation, and for forming and utilizing packed columns of beads. The present invention is particularly useful for biological sample separations.

BACKGROUND OF THE INVENTION

Column-based separations are frequently used for selectively removing components from mixtures. A first step in utilizing column-based technology is to form a column. Such can be accomplished within a column chamber. An exemplary prior art column chamber 10 is illustrated in FIG. 1. Column chamber 10 comprises a longitudinal tubular section 12 having ends 14 and 16. An inlet 18 is provided at end 16, and an outlet 20 is provided at end 14. Outlet 20 is obstructed by a porous filter 22. Filter 22 can comprise, for example, a porous fritted glass or ceramic material.

A packed column is formed within chamber 10 by flowing a slurry comprising a mixture of matrix material 15 and carrier fluid 17 into inlet 18. Matrix material 15 consists of particulates, typically spherical, with extractive or chemically selective surface. Filter 22 is permeable to the carrier fluid and impermeable to the matrix material. Accordingly, as the slurry is flowed into column chamber 10, matrix material 15 stacks against filter 22 to form a packed column 19 within tubular portion 12.

The composition of carrier fluid 17 and matrix material 15 vary depending on the components that are intended to be separated by the packed column, and on the mixtures (samples) within which such components are found. Materials that can be separated utilizing column-based systems are, for example, biological materials, such as nucleic acids. For instance, Tepnel Life Sciences supplies a resin in the form of polymeric micro-beads in diameters of approximately 60–100 micrometers which are covalently linked to specific oligonucleotide capture probes. Such micro-beads can be utilized for selective purification of nucleic acid fragments from a biological sample. Biological sample or components that may be purified on resins such as micro-beads include but are not limited to nucleic acids, peptide nucleic acids, antibodies, receptors, proteins, ligands, cells, viruses, and combinations thereof. For purposes of interpreting this disclosure and the claims that follow, the term "nucleic acid" is defined to include DNA nucleotides and RNA nucleotides, as well as any length polymer comprising DNA nucleotides or RNA nucleotides. Prior art resin includes glass, polymer (e.g. sepharose, polystyrene, etc.), metal, ceramic and combinations thereof.

Other matrix materials are Sr-resin, TRU-resin, and TEVA-resin, all of which can be obtained from EIChrom Industries, Inc., of Darien, Ill. Such matrix materials can have particle sizes in the range of, for example, 20–100 micrometers. Sr-resin, TRU-resin, and TEVA-resin can be used for, for example, selectively retaining radioactive materials. Specifically, Sr-resin can selectively retain strontium, TRU-resin can selectively retain americium, and TEVA-resin can selectively retain technetium. Slurries utilized for forming packed columns of Sr-resin, TEVA-resin, or TRU-resin can comprise, for example, 0.074 gram/mL of Sr-resin in 3 M $HNO_3$; 0.142 grams/mL of TEVA-resin in 4 M $HNO_3$; or 0.076 grams/mL of TRU-resin in 0.1 M $HNO_3$, respectively.

In addition to the above-discussed exemplary uses for column-based separations, numerous other applications for column-based separations are known to persons of ordinary skill in the art. The column-based separations generally have in common that a mixture in a first physical state (typically either a gas phase or a liquid phase) is flowed across a column matrix in a second physical state (typically either a liquid phase or a solid phase) to separate a component of the mixture from other materials of the mixture. Accordingly, the desired component or components of the mixture must be retained preferentially by the matrix while the matrix remains physically separable from all or most of the undesired mixture components.

It can be desired to quantitate and/or otherwise analyze an amount of a component retained by a column matrix in a packed column. Accordingly, it can be desired to extract a retained component from a matrix material. A method of extracting a retained component is to subject the column matrix to conditions which disrupt interactions between the matrix material and the component to thereby elute the component from the matrix material. In some applications, it is desirable to elute the retained material from the matrix material while the matrix material is still within a packed column, and in other applications it is desirable to remove the matrix material from a packed column before eluting the retained component. Additionally, there are some applications in which it is desirable to remove a matrix material from a packed column and thereafter analyze the matrix material directly to quantitate and/or otherwise analyze an amount of a component retained on the matrix material.

A difficulty in utilizing column-based separations is in removing matrix material from a column chamber and subsequently repacking additional matrix material in the chamber to re-form a packed column. There are numerous reasons for removing matrix material from a chamber. For instance, a matrix material of a packed column can be rendered unusable after an initial separation, or after an initial series of separations. A matrix material can be rendered unusable if it is degraded by fluids passed through the material during a separation. Also, the matrix material can be rendered unusable if it becomes contaminated by materials within a sample because such contamination can pose a risk of cross-contamination.

For one or more of the above-discussed reasons, it is frequently desirable to repeatedly pack and unpack a column chamber with matrix material. Because packing and unpacking of column chambers is a time-consuming and laborious process, disposable columns are generally used. However, disposable columns still require manual or robotic labor for column changeout. Accordingly, it is desirable to develop new methods for packing and unpacking column chambers.

A recent improvement is described with reference to an apparatus 30 in FIGS. 2 and 3. Referring to FIG. 2, apparatus 30 comprises a tubular column chamber 32 having an inlet end 34 and an outlet end 36. Outlet end 36 terminates in close proximity to a plate 38. Plate 38 can comprise a window configured to enable light to pass through for spectroscopic measurement of materials eluting from column chamber 30. A matrix material 40 forms a packed column 42 within column chamber 32. Packed column 42 has a lateral periphery defined by tubular chamber 32. Packed column 42 can be formed by flowing a slurry of matrix material 40 and a carrier fluid into column chamber 32. Outlet end 36 of column chamber 32 is displaced from plate 38 by a distance "D" sufficient to enable the carrier fluid to pass between column chamber 32 and plate 38. However, the distance is less than an average width of matrix material 40. Accordingly, matrix material 40 is retained in column chamber 32 and stacks against plate 38 to form packed column 42.

FIG. 3 illustrates a system 30 for removal of matrix material 40 from packed column 42. Specifically, column chamber 32 is raised to enable matrix material 40 to pass beneath column chamber 32 and over plate 38. Subsequently, a fluid is flowed through chamber 32 to push matrix material 40 out of column chamber 32.

System 30 is improved relative to other methods of packing and unpacking columns in that it can provide a quick method for releasing packed column material from a column chamber, and can also provide a quick method for resetting the column chamber to be repacked with fresh matrix material. Most importantly, no permanently installed porous material is used to retain matrix material in a fluid stream. Porous material such as filter 22 in column 10 can clog by embedding relatively small particles from the matrix or mixture. A difficulty with column system 30 is that it can be problematic to move an entirety of column chamber 32 during transitions between packing and unpacking operations. Further, precise alignment is required to hold beads in the column. Discharged beads can undesirably pass through a detector. It can become increasingly difficult to move the entirety of column chamber 32 as a column-based separation is scaled up for larger operations. Accordingly, it is desirable to develop alternative methods for conveniently packing and unpacking column chambers, wherein a column chamber is not moved in transitioning between packing and unpacking operations.

An alternative embodiment is shown in FIGS. 4a, 4b using an axially moveable solid rod 400 instead of the column chamber 32. In this alternative embodiment, the tolerance between the outside dimension of the rod 400 and the inside dimension of the column chamber 32 is one half a bead diameter. A disadvantage of this embodiment is that the inserted portion or surface is alternately wetted and not wetted as it is inserted and withdrawn. A similar, alternately wetted and not wetted surface exists for column chamber 32 (FIG. 3). These inserted surfaces provide an opportunity for sample carryover into a subsequent sample. This is especially critical for DNA analysis wherein a very small carryover from a previous sample can be detected in a subsequent sample. A related concern is that relatively small, abrasive particles may abrade or grind the alternately wetted and not wetted surface within the tightly pressed interface during actuation.

SUMMARY OF THE INVENTION

This invention is an apparatus and method of packing and unpacking a column chamber by alternately retaining and releasing a packed column in a fluid stream. A mixture of a fluid and a matrix material are introduced through a column chamber inlet so that the matrix material is packed within a column chamber. Once packed, the column may be used for purposes including but not limited to chemical extraction, titration, chemical sensing, filtration or combinations thereof. Uses generally involve the flow of a fluid mixture or carrier through the retained, packed column. After use, the matrix material is unpacked from the column chamber without removing the column chamber. More specifically, the column chamber having the column chamber inlet or first port for receiving the mixture further has an outlet port which is alternately restricted or open with respect to matrix material but always open with respect to fluid flow. When restricted, matrix material is retained; and when unrestricted or open, matrix material is released so that it can be ejected fluidically from the column chamber. The outlet port is alternately restricted or unrestricted with respect to the matrix by rotation relative one to the other of a rod with a binary end placed in the outlet port.

An advantage of the rod with the binary end is that the surface area of the rod in contact with fluid is always in contact with the fluid stream or the interior of the column chamber. In other words, there is no rod surface area that alternately contacts fluid then, say, an interior surface of the column chamber. This feature minimizes the potential of sample to sample contamination since a sample may be completely washed through and not captured on an alternately or intermittently exposed surface. This is especially valuable for nucleic acid or DNA samples wherein one molecule of a previous nucleic acid sample can be detected in a subsequent nucleic acid or DNA sample. A related aspect of this feature is the absence of any surface which is alternately a press-fitted interior surface and a fluid-contacting surface. This feature precludes the potential for abrasion by relatively small matrix or mixture particles carried by the alternating surface.

Isolation of nucleic acids from environmental samples such as soil is especially challenging because the co-extraction of metals, chelators, humic acids and other organic contaminants will interfere with downstream molecular biology procedures such as polymerase chain reaction (PCR). An advantage of the present invention is avoidance of co-extraction by using affinity matrix microparticles that selectively retain nucleic acids of interest but exclude all other soluble soil constituents.

The rod with a binary end also satisfies the need to alternately retain and release matrix material in a fluid stream without resorting to any permanently installed filter material which can clog by embedding particles.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

Preferred embodiments of the invention are described below with reference to the following accompanying drawings.

FIG. 5d is a view of a rod with a stepped binary end.

FIG. 5e is a top view of a straight stepped binary end.

FIG. 5f is a top view of a cup stepped binary end.

FIG. 5g is a top view of a yin-yang stepped binary end.

FIG. 5h is a cross section of a through wall hole chamfer.

FIG. 5i is a cross section of a wall to end hole chamfer.

FIG. 5j is a view of a concave stepped end.

FIG. 5k is a view of a convex stepped end.

FIG. 5l is a view of a multi-stepped end.

FIG. 7a is a cross section of an alternative embodiment in the closed position.

FIG. 7b is a cross section of an alternative embodiment in the open position.

FIG. 8a is a cross section of a side penetrated embodiment in the closed position.

FIG. 8b is a cross section of a side penetrated embodiment in the open position.

DETAILED DESCRIPTION OF THE PREFERRED EMBODIMENTS

Figure 1:
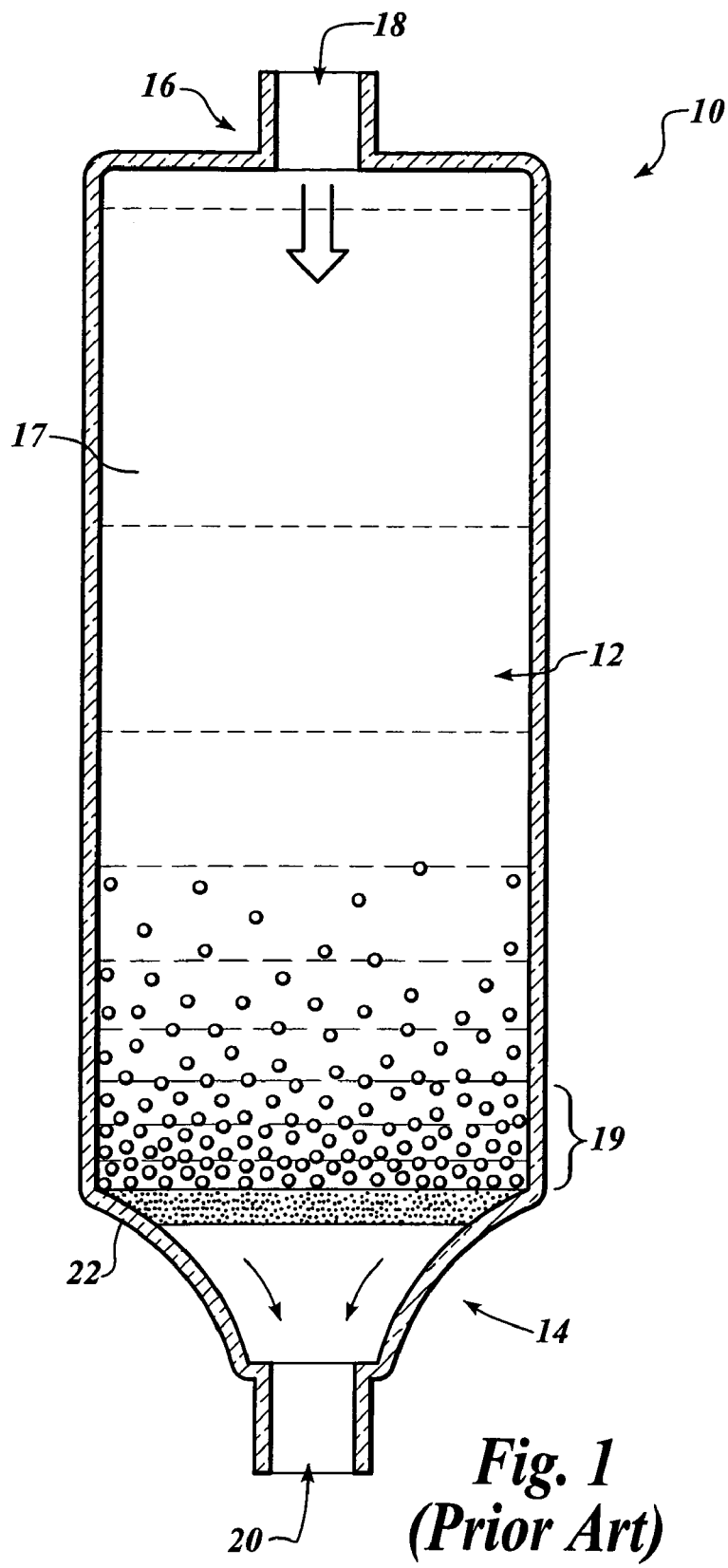
FIG. 1 is a diagrammatic, cross-sectional view of a prior art column construction.
Figure 2:
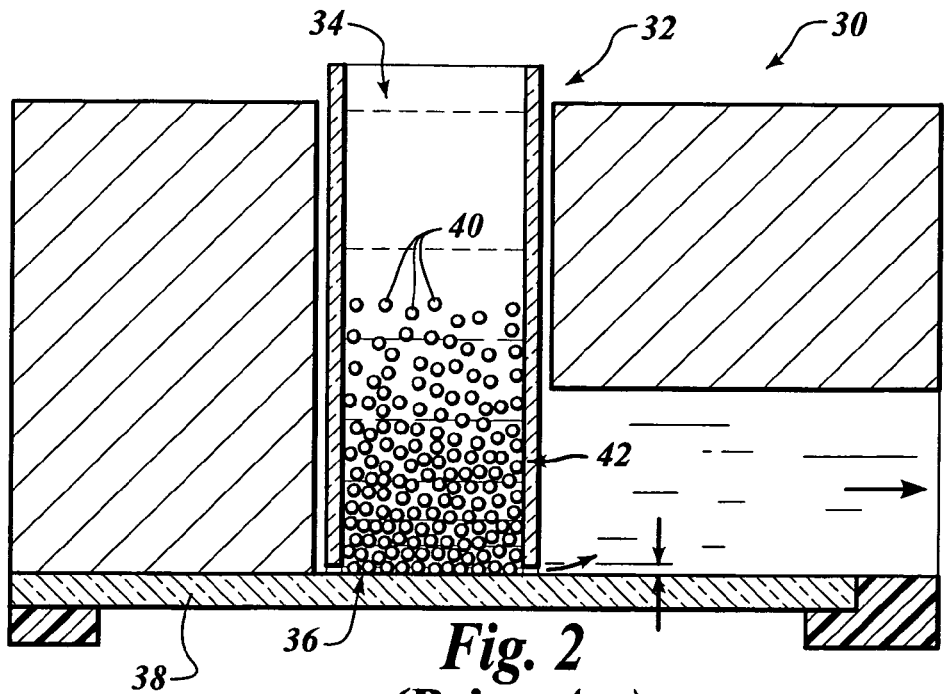
FIG. 2 is a diagrammatic, cross-sectional view of a prior art system for packing and unpacking a column chamber. The system of FIG. 2 is shown with the column chamber in a position for packing a matrix material within the column chamber.
Figure 3:
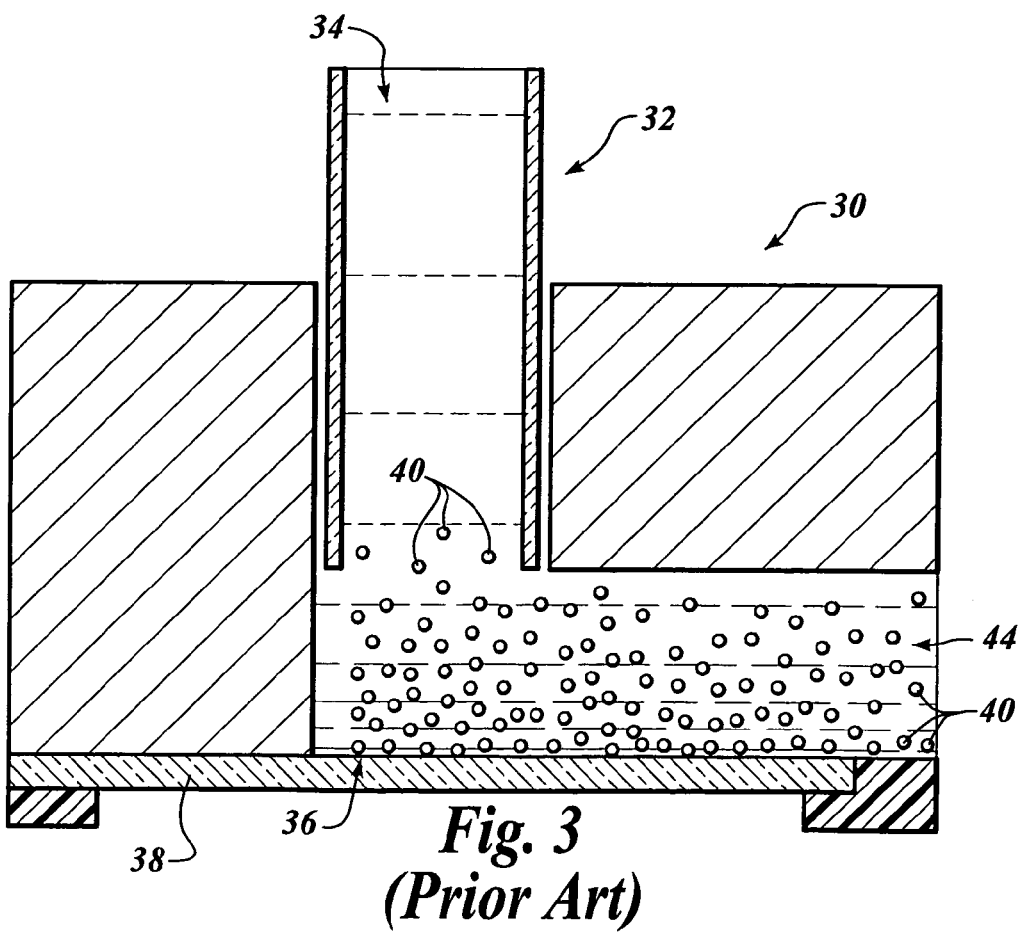
FIG. 3 is a view of the FIG. 2 system, with the column chamber shown in a position for unpacking the column chamber.
Figure 4A:
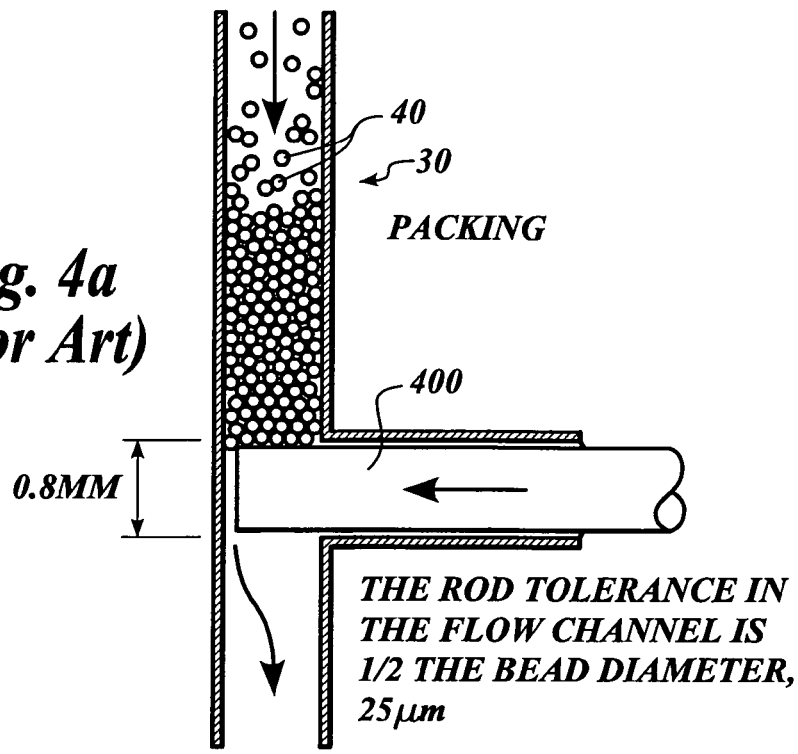
FIG. 4a is a view of a prior art column chamber controlled with an inserted rod that is axially actuated, closed position.
Figure 4B:
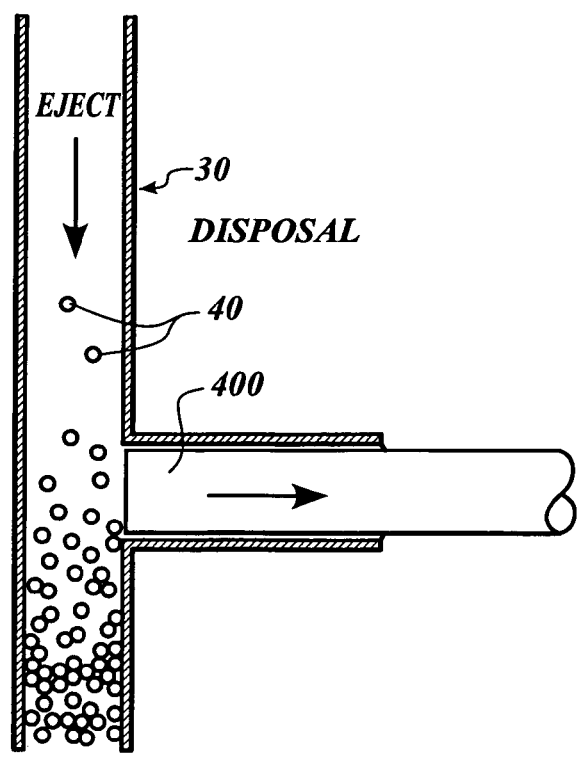
FIG. 4b is a view of a prior art column chamber controlled with an inserted rod that is axially actuated, open position.
Figures 5A, 5B, 5C:
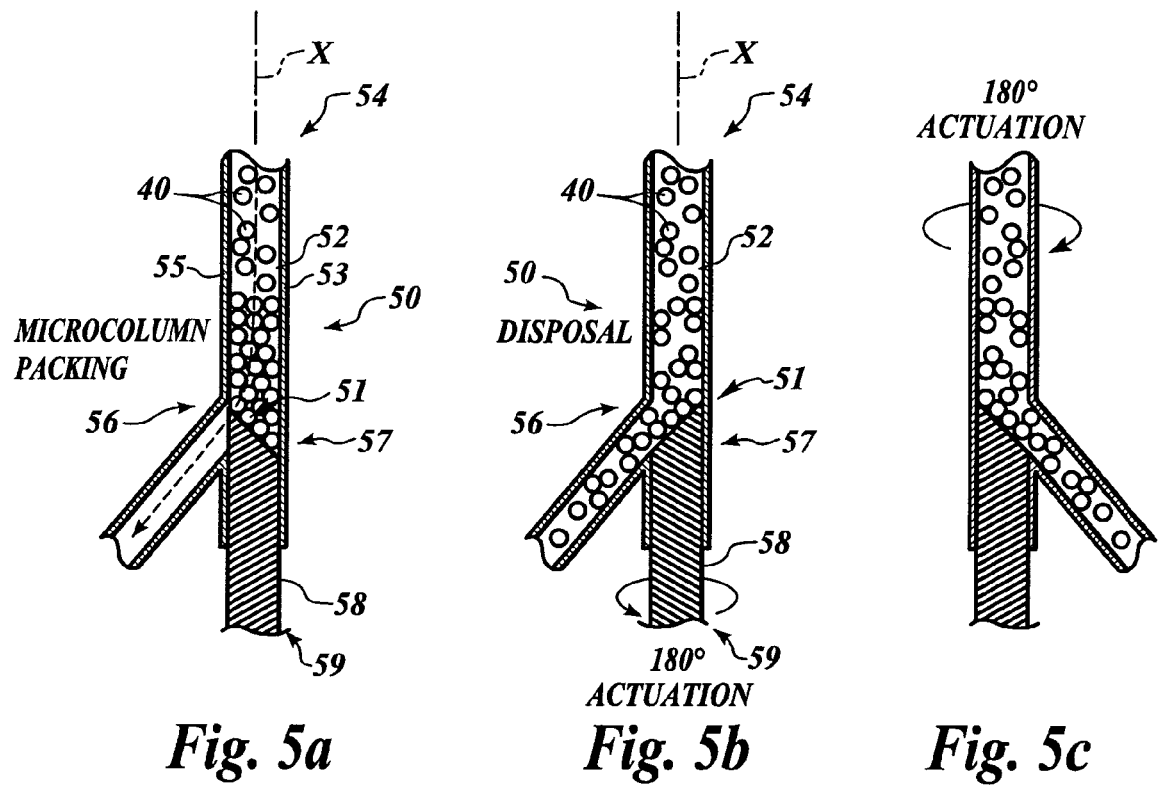
FIG. 5a is a view of an embodiment of the present invention having a rod for controlling matrix material flow, closed position.
FIG. 5b is a view of an embodiment of the present invention having a rod for controlling matrix material flow, open position, chamfered rod rotated.
FIG. 5c is a view of an embodiment of the present invention having a rod for controlling matrix material flow, open position, column chamber rotated.

The invention encompasses systems for column based separations configured to pack and unpack column chambers using a rotateable rod with an asymmetric end for trapping and releasing matrix material. Referring to FIGS. 5a, 5b, and 5c, a system 50 for column-based separations comprises a column chamber 52 having an inlet end 54, an outlet end 56, and an actuator end 57. Column chamber 52 comprises a longitudinal axis "X", and can be formed of, for example, glass, plastic or metal. In the shown cross-sectional sideview (FIG. 5a), column chamber 52 comprises a pair of opposing sidewalls 53 and 55. Although sidewalls 53 and 55 are shown as physically separated in the shown cross-sectional view, it is to be understood that sidewalls 53 and 55 can be portions of a continuous periphery. For instance, column chamber 52 can have a cylindrical shape, with sidewalls 53 and 55 forming portions of a continuous circular periphery of the cylinder.

Outlet end 56 is alternately partially obstructed and opened with a rod 58 having a binary end 51 which is inserted into the actuator end 57. The rod 58 has a surface that is non-absorbent of the sample. Possible rod materials include but are not limited to metal, plastic, plastic coated metal and combinations thereof. The rod 58 has a first end or binary end 51 and a second end 59. By "binary" we mean that the rod end has an asymmetric feature with respect to a rotation about its longitudinal axis such that a restriction gap is present in one angular rod orientation and an unrestricted gap in another orientation. The restriction gap is small enough so that matrix material cannot pass but large enough so that fluid can pass. Infinitely many shapes constitute such a binary end of which the preferred embodiment is the simplest geometry (shown in FIGS. 5a, 5b, and 5c). Other example binary rod include but are not limited to the geometries are shown in FIGS. 5d–5l and combinations thereof. In all cases, the rod 58 is inserted into an actuator port 57 to a position wherein the binary end 51 of the rod 58 is situated at the intersection of the column chamber 55 and outlet 56; and the second end 59 extends beyond the actuator port 57 where it may be connected to a mechanical actuator (preferred), or operated by hand.

The size of the annulus between the outside surface of the rod 58 and the inside surface of the outlet 56 that allows fluid flow but traps the matrix material 40 when the rod is in the closed position (FIG. 5a) is controlled by either adjusting the diameter of the rod, or by adjusting the column diameter. In the preferred embodiment shown in FIG. 5a, the diameter of the column inlet 54 is slightly larger than the diameter of the rod 58, so that the annulus is about 20–30 micrometers. The matrix material 40 is preferably in the form of beads that are larger than the annulus. In preferred methods of the present invention, a slurry comprising a liquid carrier fluid and a matrix material is injected into column chamber 52. The liquid carrier fluid then flows through outlet 56, while the matrix material is retained by the chamfered end 51 of rod 58.

The system 50 described with reference to FIGS. 5a, 5b, and 5c, can be shifted from a packing mode to an unpacking mode by activating (rotating) either the rod 58 or the column chamber 52 with respect to the other. Specifically, when rod 58 is in a closed position, system 50 is in a column chamber packing mode (FIG. 5a), and when rod 58 is in an open position, system 50 is in a column chamber unpacking mode (FIG. 5b). During discharge of matrix material, a fluid, preferably a liquid, is flowed through the column chamber to flush matrix material from column chamber 52. The fluid flowed during discharge of matrix material can be referred to as a dislodging fluid, and can be the same as the carrier fluid.

Figure 6:
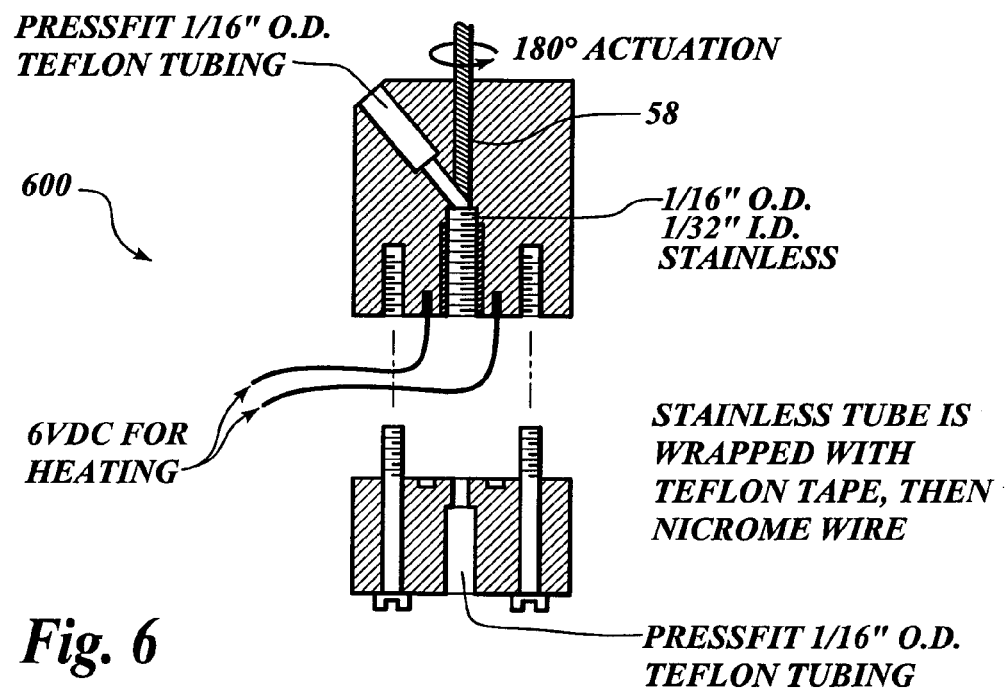
FIG. 6 is a cross section of a block supported system with temperature control.

In FIG. 6, a support structure 60 is provided to system 50. Support structure 60 can comprise, for example, a plastic material molded or machined to fit system 50. Alternatively, support structure 60 can include, for example, a clamp. The support structure 60 may further include a heater 62 for temperature control of the sample. The heater may be any heater including but not limited to fluid heat transfer (jacket), electric resistance heater, combustion heater and combinations thereof. A preferred heater is a resistance heater of stainless steel tube wrapped with Teflon (polytetrafluoroethylene) tape and wound with a nichrome wire encapsulated by a layer of thermally conducting, electrically insulating epoxy.

Temperature control may be a critical feature for sample handling of biomolecules including but not limited to DNA, protein and combinations thereof. Elevated temperature can help to purify a sample by excluding interferents either during analyte extraction from a sample or during a subsequent wash step. For example, the perfectly matched DNA sequence of a target DNA provides one of the strongest binding interactions between the matrix material and a component of the sample. Elevated temperature challenges binding of sample components so that only the strongest binding interactions, like that of the target DNA, succeed. Further, an increase in temperature above the capture temperature may be used to elute biological molecules from the matrix material. Heating to a temperature above the capture temperature changes the conformation (shape) of biomolecules and affects the binding equilibrium of ligands with the biomolecules. Hence, the increased temperature may be used, for example, to remove ligands from antibodies, remove ligands from receptors, and remove DNA from complementary DNA or DNA chimeras (e.g. PNA).

Because a metallic column chamber may introduce metal ions into the sample, it may be necessary to substitute a polymer, for example polyethyletherketone (PEEK) that is inert to the sample at the higher temperatures.

Once a nucleic acid sample is obtained by any of the above discussed procedures or by another procedure, it may be processed by polymerase chain reaction (PCR). The PCR may be carried out in a column chamber (with or without the rod) using the temperature control for thermal cycling for the PCR.

In addition to the preferred embodiments, the present invention encompasses further embodiments. For example in FIGS. 7a and 7b, the outlet and inlet are reversed compared to FIGS. 5a, 5b and 5c. In cases wherein the matrix material 40 is in the form of beads smaller than the annulus (for example PNA derivatized 20 micrometer Poros™), larger inert material (not shown), for example glass beads, may be inserted ahead of the matrix material 40 to capture the matrix material 40.

The angle between inlet 54 and outlet 56 may be varied.

In FIGS. 8a and 8b, the rod 58 penetrates the side of the column chamber 50 rather than the end of the column chamber 50.

The column chamber is preferably packed and unpacked with matrix material while flowing fluids through the column chamber 50 in an identical flow direction during both the packing and unpacking operations. Specifically, all, or at least most, of the matrix material is preferably expelled from a column chamber along an identical flow direction as was utilized to pack the column chamber. However, it is to be understood that the invention also encompasses embodiments in which flow of fluid through a column chamber is reversed during a packing or unpacking operation. Preferably, the flow during a packing operation will not be reversed, but will instead be continuous in a flow direction from an inlet of the column chamber through an outlet. Also preferably, a flow of fluid through a column chamber will be predominately in a single direction from an inlet of the column through an outlet of the column during an unpacking operation. However, the unpacking operation can preferably also comprise some sporadic instances wherein flow is reversed (i.e., to go from an outlet to an inlet) to assist in dislodging matrix material from within column chamber.

Embodiments of the present invention can be operated with a vast number of matrix materials, as will be appreciated by persons of ordinary skill in the art. Example classes of matrix materials include but are not limited to polymer, glass, metal ceramic and combinations thereof. Specific examples of matrix materials include but are not limited to sepharose, polystyrene, polyethylene glycol/polystryrene, zirconium, and hydroxyapatite as well as brand name resins such as POROS and Qiagen. Suppliers of materials for biological separations include but are not limited to Tepnel Life Sciences and PerSeptive Biosystems. Many of these resins can be derivatized to contain specific functional groups such as antibodies or oligonucleotides which can be used to bind specific biological materials onto the resin material. Biological materials include but are not limited to viruses, both prokaryotic and eukaryotic cells, nucleic acids, proteins, other biomolecules and combinations thereof. Certain matrix materials are materials for specifically separating nucleotide fragments (e.g., nucleic acid, DNA, RNA or combinations thereof) based upon a sequence of the fragments, such as, for example, the Tepnel micro-beads discussed above in the Background section of this disclosure. The Sr resin, TRU-resin, and TEVA-resin described above in the Background section of this disclosure, can be utilized for separating radioactive molecules or atoms from other materials in the sample.

Nucleic Acid Separation and Purification: Apparatus and Methods

In an example method of the present invention, column 50 is packed with a matrix material 40 that selectively binds nucleic acid fragments. Biological samples are prepared for separation on column 50 by lysing cells to form a lysis suspension. Insoluble debris is then removed from the lysis suspension by, for example, centrifugation and/or filtration to form a solution which is then passed through column 50 across the matrix material 40. Nucleic acid fragments within the sample are then selectively bound to the matrix material 40. Such nucleic acid fragments can be subsequently eluted from the matrix material 40 by methods known to persons of ordinary skill in the art, such as, for example, passing a solution comprising a low salt concentration across the matrix material 40.

An apparatus (FIG. 8) comprising a readily repackable column chamber 50 can have particular utility for purifying biological samples, as it is frequently difficult to completely regenerate a column 50 after such purification, and as the amount of material obtained is so small that even a minor amount of cross contamination can be problematic.

EXAMPLE 1

PCR was used to evaluate the effectiveness of the separation and purification system for extracting a specific bacterial DNA (*Geobacter chapellii*) from a salt solution 9 and also from a crude soil extract that contained a background of $10^8$–$10^9$ genomes within 200 μl, as well as humic acids and other organic material. When compared to manual benchtop extraction methods using the same reagents, the automated separation and purification system is faster (12 minutes versus several hours), and the extraction efficiency obtained using the automated extraction system is equivalent to benchtop methods using the same reagents.

Figure 9:
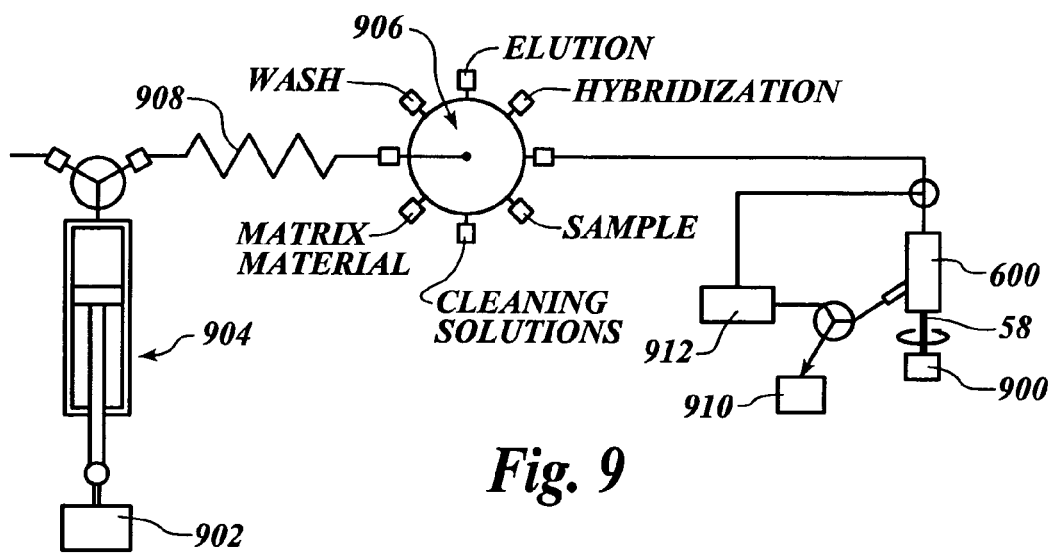
FIG. 9 is a schematic view of a sample treatment apparatus of the present invention.

Sequential Injection Analysis (SIA) is well known in the analytical chemistry literature as a pump and valve configuration and its associated fluid handling procedure for performing wet chemical analyses. FIG. 9 diagrams the DNA extraction purification apparatus comprising a sequential injection system and the preferred embodiment temperature controlled column chamber 600. The pumps and valves are preferably operated under computer control to automate the packing and disposal of the matrix material. Where only pumps and valves are used, the computer is capable of using a WINDOWS™ environment with preferred software FIALab™ for WINDOWS™. However, addition of a stepper motor 900 for turning the rod, addition of heating elements for temperature control along with a thermocouple for measuring temperature are outside the scope of FIALab. Thus, the software needed to control an automated procedure may be written in any computer programming language, for example Visual Basic. FIALab commands are still incorporated into the preferred programming environment by using an ActiveX™ version of FIALab. Procedural steps to implement the sequence and timing of operations are entered into the software.

A second stepper motor 902 may be used for controlling the syringe pump 904. and selection valve were obtained as a unit from Alitea™ USA. The stepper motor controlled syringe pump 904 is connected to the common port of a selection valve 906 via a coiled length of tubing 908. The coiled tubing (holding coil) 908 is used as a reservoir for holding a sample, extraction material or reagents. In each step of the sequential injection procedure, a liquid or slurry is aspirated into the holding coil 908 via a selected valve port, then the valve is switched to the column chamber port and the coil contents are injected into the column 600. Air separators prevent bead slurry, sample and other solutions from mixing or dispersing.

As in prior art, a sequence of injections into the column chamber 600 packs the column chamber 600 with matrix material 40, perfuses the matrix material 40 with sample and reagent, and then disposes of matrix material 40 to a detector or to waste 810. For example, the first step in the preferred procedure is to aspirate matrix material slurry into the holding coil 908, switch the valve 906 to the column chamber port and inject the slurry into the column chamber 600. The binary end of the rod 58 in the column chamber 600 is in the closed position to retain the matrix material while allowing fluid to pass so that a packed column is formed. Similar back and forth motions of the syringe pump 904 coordinated with valve 906 selection allows for injection of sample, wash, eluent, and chemical cleaning agents as well as disposal of the used or spent matrix material. A recirculating pump 812 may be used for multiple passes of fluids through the column chamber 600.

When used for DNA extraction, for example with DNA extraction solutions listed in Table 1, the automated DNA extraction procedure described above is used with the apparatus described above as outlined stepwise in Tables 2 through 4.

TABLE 1

Solutions used for DNA Extraction (FIG. 9 apparatus)

| | |
|---|---|
| Matrix material slurry: | 15 mg/ml 1392r-Tepnel beads in 0.3 M NaCl |
| Hybridization solution: | 0.2 M NaPO4, 0.1 M EDTA, 0.25% SDS |
| Sample: | a) 200 μl crude soil extract with 100 ng *Geobacter metallireducens* DNA or |
| | b) 200 μl hybridization solution with 100 ng *Geobacter metallireducens* DNA (sheared to 4–10 Kbp). |
| Wash solution: | 0.5X SSC [0.15 M NaCl, 7.5 mM NaCitrate, pH 7.0] |
| Eluent: | Water |
| Zap component 1 ** | |
| Zap component 2 ** | |

Tables 2–4 represent stages of one complete procedure which requires 12 minutes to complete. In order to make the procedure readable, standard implementation details were omitted, namely the use of 10 μL air separators between fluids, and loading of fluids into the holding coil prior to each injection. Table 2 lists the first sequence of injections into the flow cell ending with the elution of purified DNA. The flow cell is in the closed position throughout the Table 2 sequence; and the matrix material must be stirred into fluid suspension to create a "bead slurry" for the first injection. Tables 3 and 4 outline cleaning procedures after the extraction. All steps in Table 3 are performed at 50 μL/s. All steps involving DNA Zap reagents (Ambion, Inc. Austin, Tex.) in Table 4 are performed at 10 μL/s except for water rinsing steps, which were 50 μL/s.

Table 4 refers to a set of stacked DNA Zap reagent zones. Throughout the preferred DNA extraction procedure, air separators keep fluids from mixing as they are aspirated into the holding coil and injected into the cell. However, in the Table 4 procedure air separators are omitted between the two DNA Zap reagents because these are deliberately mixed. When the two DNA Zap reagents are mixed, they form a short-lived intermediate chemical species that destroys DNA. Mixing is achieved in the sequential injection system by alternately aspirating short segments of each reagent into the holding coil. This is termed a "stacked zone" of reagents that are mixed by dispersion when flowed through tubing.

TABLE 2

Sequence of Injections into the Column Chamber for Matrix Packing and DNA Extraction (FIG. 9 apparatus)

| solution | injection volume/μL | flow rate/ (μL/s) | temperature/ ° C. |
|---|---|---|---|
| slurry | 113 | 10 | (no heating) |
| hybridization | 50 | 10 | ramp up to 60 |
| Nucleid acid sample solutions were heat denatured at 100° C. for 5 min. and quick-chilled on ice immediately before aspiration into the system. | | | |
| sample | 200 | 1 | 60 |
| wash | 60 | 3 | 45 |
| {stop flow. Ramp up to 85° C.} | | | |
| eluent | 40 | 1 | 85 |

TABLE 3

Disposal of the Packed Matrix Material (FIG. 9 apparatus)

| | |
|---|---|
| step 1: | Aspirate 35 μL from the flow cell to pull matrix material particles away from the binary end of the rod. |
| step 2: | Rotate the rod to the open position. Optional: aspirate another 20 μL to disperse the bead material into fluid suspension. |
| step 3: | Eject the beads to waste by injecting 200 μL of water through the cell. |

TABLE 4

Chemical Destruction of Residual DNA in the Flow System (FIG. 9 apparatus)

| | |
|---|---|
| step 1: | Aspirate stacked zones of DNA Zap reagent into the holding coil 10 μL further than the volume of sample used. |
| step 2: | Push the DNA Zap reagent back out of the holding coil and into the (currently empty) sample inlet until it completely fills the sample inlet. |
| step 3: | Switch the valve to the flow cell, and push the remaining DNA Zap reagent into the column chamber. |
| step 4: | While the DNA Zap remains in the inlet and column chamber, aspirate another set of DNA Zap stacked zones into the holding coil. |
| step 5: | Switch to the sample valve position and aspirate the previous DNA Zap mixture from the sample inlet into the holding coil behind the fresh mixture of DNA Zap. Again, aspirate to the point 10 μL further than the volume of sample used. |
| step 6: | Inject all DNA Zap to waste through the column chamber. |
| step 7: | Rinse the sample inlet and column chamber with water. |

The matrix material used for the on-line affinity purification of DNA was obtained from Tepnel Life Sciences (Cheshire, England) and included universal 16S rRNA oligonucleotide 1392r with a $dT_8$ linker (lower case) covalently attached to 60 µm polystyrene microbeads (bead-5' tttttttt-tACGGGCGGTGTGTRC). The binding capacity was estimated to be 2 pmol $mg^{-1}$ (or $cm^2$) beads ($1.20 \times 10^{12}$ probes $mg^{-1}$) based upon a competitive hot/cold assay using complementary oligonucleotides (Tepnel). This universal oligonucleotide sequence will capture all types of bacterial DNA on the column, and dilution to extinction PCR analysis may be used to specifically detect *Geobacter metallireducens* DNA that is eluted from the column.

Figure 10:
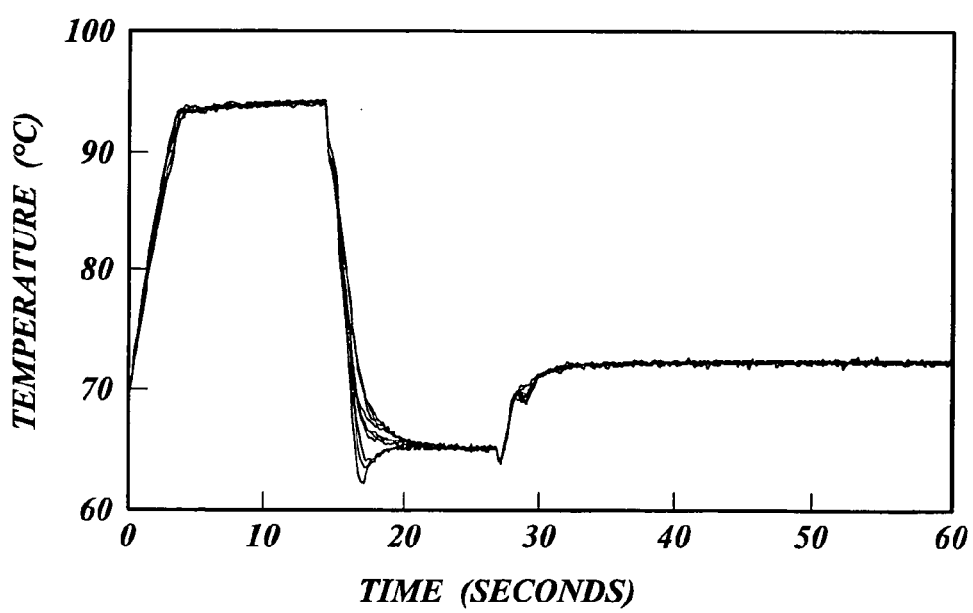
FIG. 10 is a graph of temperature versus time demonstrating precise temperature control for the present invention.

The DNA extraction procedure outlined in Tables 2–4 requires temperature control of the column matrix 50. FIG. 10 shows 10 replicate thermocycles performed in the column chamber used for DNA extraction. This data was collected using a type-K thermocouple in the column chamber which was filled with aqueous solution. A feedback control algorithm achieved the sequence of targeted temperatures, 93, 65, and 72° C. These temperatures and durations are suitable for PCR amplification of DNA.

Temperature control may be achieved during the DNA extraction without the intrusion of a thermocouple probe. This was done by first using intrusive measurement and feedback control to obtain a voltage vs time function that achieved the desired sequence of temperatures at the proper flow rates of the extraction procedure. The resulting voltage vs time were recorded so that they were executed in future DNA extraction procedures as a substitute for feedback control. The temperature curves achieved in this way were found to be similar to those of feedback control.

A more robust method of temperature control is to use non-intrusive temperature measurement with feedback control. This can be achieved by using a resistance heater that also serves as a resistance temperature detector (RTD). For example, a resistance coil of nickel has a suitably high temperature coefficient of resistance. The temperature dependent coil resistance can be determined from the applied voltage and resulting current. The temperature can be determined in real-time once the calibration relationship is established between heater coil resistance and column temperature. The calibration points would be coil resistance and temperature data pairs over stable plateau regions such as those of FIG. 10.

EXAMPLE 2

An experiment was conducted to demonstrate a DNA extraction according to the present invention. Genomic *Geobacter metallireducens* DNA was sheared to 4–10 Kbp in size by ballistic disintegration for 1 minute at 5000 oscillations $s^{-1}$ in an 8-place bead beater (BioSpec Products, Inc., Bartlesville, Okla.) with 12 µg DNA, 0.75 g 0.1 mm glass beads and 500 µl water.

Nucleic acid extracts were prepared from a garden soil by aliquoting 12×0.5 g soil into 2.0 ml screw-cap microfuge tubes containing 1.5 g 0.1 mm glass beads and 1 ml extraction buffer [0.2M $NaPO_4$, 0.1M EDTA, 2% SDS, pH 8.0]. Slurries were frozen at −80° C. for 1 hr, thawed at 65° C. for 30 min. and cells lysed by ballistic disintegration at 5000 oscillations $s^{-1}$ for 2 min. Glass beads, sediment and cell debris were removed by centrifugation at 14,600×g for 10 min. at 18° C., and the supernatants pooled. Crude extracts were dialyzed against several changes of sterile water, passed through a 0.2 µm syringe-filter and the salt concentration adjusted to 0.3 M NaCl. The sodium ion concentration of the soil extract was adjusted to 0.3 M to provide solution conditions comparable to those normally encountered in solution hybridization studies, standard membrane hybridizations and sequence-specific purification systems based on oligo-dT or biotinylated oligonucleotides and streptavidin-coated paramagnetic particles. Due to spectroscopic interference by humic acids and other soil constituents, total DNA in the crude soil extract was quantified by ethidium bromide staining after gel electrophoresis. Temperature control was achieved during the DNA extraction without the intrusion of a thermocouple probe.

The estimated nucleic acid concentration in 200 µl of crude soil extract was 3 µg, or $6 \times 10^8$ cell equivalents of genomic DNA.

Figure 11:
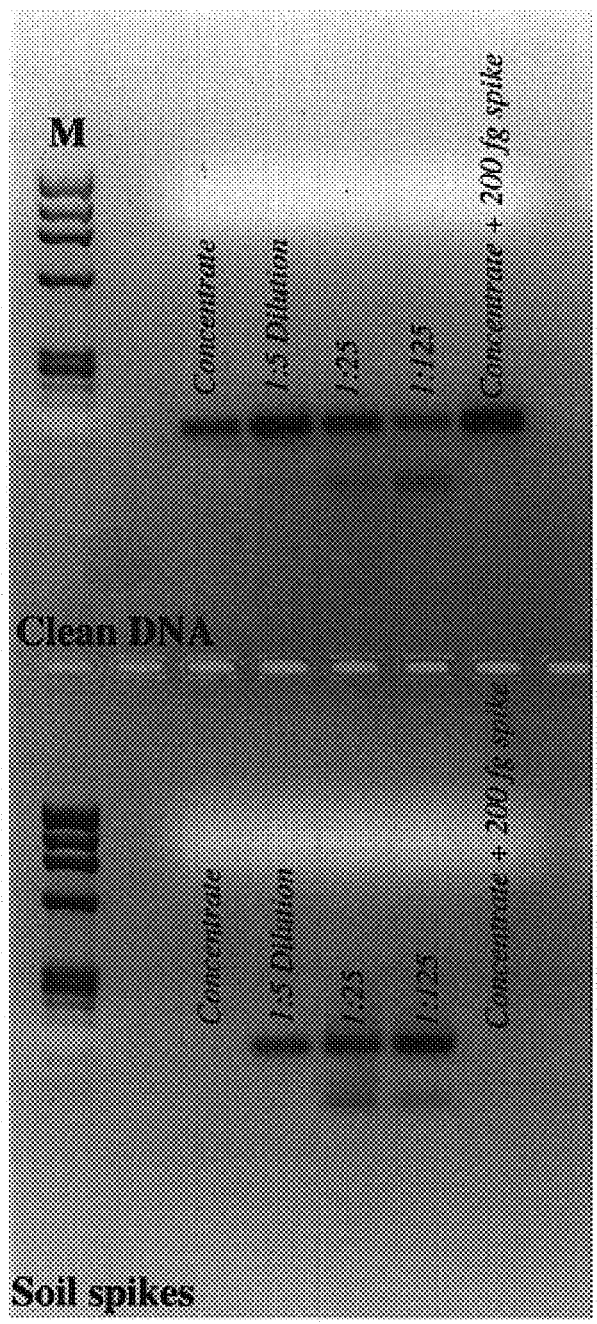
FIG. 11 is a PCR dilution series of the eluant obtained from the automated DNA purification from a spiked salt solution (top) and a spiked soil extract (bottom) using the temperature controlled renewable column system shown in FIG. 9, and the procedure described in Tables 1–4. Gel electrophoresis with ethidium bromide staining was used to detect the PCR product. Concentrate indicates a 2-fold concentration of the eluant, and dilutions of this concentrate are indicated in each lane.

FIG. 11 shows a PCR dilution series for the specific capture of *Geobacter metallireducens* DNA in salt solution (top) and a soil extract (bottom) using the automated system. The automated capture procedure is outlined in Tables 1–4. The eluant was lyophilized to dryness and resuspended in 20 µl of water prior to PCR. Since the salt solution used for the "Clean DNA" extraction does not contain PCR inhibitors, *Geobacter metallireducens* is detected by PCR at all dilutions shown in the top of FIG. PCR inhibitors were present in the 2-fold concentrated eluant (FIG. 11), bottom, concentrate and concentrate+200 fg spike), but not in the lanes with additional dilution (FIG. 11, bottom, 1:5, 1:25, 1:125). This is a positive result since it indicates that most of the PCR inhibitors are removed during the purification process, and therefore PCR can be used to detect DNA as long as the sample is not concentrated prior to PCR. Without purification, the *Geobacter metallireducens* spiked into the crude soil extract is not detectable by PCR.

The automated DNA extraction methods described in these reduction to practice experiments represent a significant improvement in processing time compared to manual DNA extraction procedures from soil. The total processing time for the automated extraction described above is 12 minutes, however, the manual extraction procedure typically requires 1 to 5 hours to complete (depending on the batch hybridization reaction time).

Radiological Separation and Purification: Apparatus and Methods

Although DNA extraction was used to demonstrate the utility of the apparatus for renewable column separation and purification described in this patent application, extraction procedures using packed column and renewable column prior art can generally be adapted using the present invention to provide additional renewable columns for chemical sample separation and purification according to the present invention. Chemical sample includes but is not limited to radioactive atom, chemical species, lipid and combinations thereof. The invention may specifically be used as a renewable column to separate radionuclides from nuclear waste samples. A proposed protocol is outlined in Tables 5 through 7, and a proposed system is as shown in FIG. 8 absent the recirculating pump and absent temperature control. It is preferred that the column height of matrix material be increased for radiological separation. The present invention would be advantageous when using samples and/or affinity matrix materials that contain particulates that might clog a frit.

TABLE 5

Packing of Americium Extraction Column

Step# Event (Flow Rate)

1. Aspirate 100 μL of air into the holding coil (15 mL/min)
2. Aspirate 635 μL of carrier into a syringe (35 mL/min)
3. Aspirate 700 μL of sorbent slurry into the holding coil (3 mL/min)
4. Dispense 700 μL of sorbent slurry to column chamber via the packing line (3 mL/min)
5. Repeat steps 4 and 5 three times
6. Dispense 635 μL to the packing line (3 mL/min). Pause 12 seconds.

TABLE 6

Extraction Purification Sequence for Americium

Step# Description: Reagent (Flow Rate)

2. Condition column: 1.5 mL 2M $HNO_3$ (1.0 mL/min)
3. Load sample: Inject 100 μL sample (1.0 mL/min)
4. Wash column: Inject 6 mL 2M $HNO_3$ (1.0 mL/mm)
5. Switch the two-way valve to "detector"
6. elute Am: 4 mL 3M HCl (1.0 mL/min)
7. elute actinides: 4 mL 0.1M ammonium bioxalate (1 mL/min)

TABLE 7

Disposal of the Americium Extraction Column

Step# Event (Flow Rate)

1. Switch the two-way valve to the "save beads" position, and switch the selection valve to the "packing" position
2. Aspirate 150 μL through the closed column chamber to move beads away from the binary end of the rod (12 mL/min)
3. Open the column chamber and aspirate another 150 μL to disperse beads into fluid suspension (12 mL/min)
4. Inject 1000 μL of water through the column chamber to eject beads to the "save beads" container

CLOSURE

While a preferred embodiment of the present invention has been shown and described, it will be apparent to those skilled in the art that many changes and modifications may be made without departing from the invention in its broader aspects. For example, a second outlet (not shown) may be added below the binary end so that the second outlet is a fluid outlet only. The original outlet in cooperation with the binary end permits packing and unpacking of the matrix material. The appended claims are therefore intended to cover all such changes and modifications as fall within the true spirit and scope of the invention.

The invention claimed is:

1. A method of packing and unpacking a column chamber, comprising the steps of:

flowing a mixture of a matrix material and fluid into a column chamber having a rod in a first position and forming a packed column from the matrix material, said column chamber having a first port for receiving said mixture, an outlet port and an actuator port wherein said actuator port is provided as having said rod having a binary end placed within said actuator port wherein said binary end of said rod blocks the flow of said matrix material to said outlet port in said first position, permits the flow of said matrix material to said outlet port in a second position, and maintains contact with said fluid flow and allows the flow of said fluid through said outlet port in all positions;

capturing said matrix material and permitting said fluid to flow therepast by positioning said binary end of said rod in said first position; and opening said outlet by positioning said binary end of said rod in said second position, thereby permitting said matrix material and said fluid to flow through said outlet port thereby unpacking the matrix material from the column chamber.

2. The method of claim 1 wherein the unpacking removes substantially all of the matrix material from the column chamber.

3. The method of claim 2 wherein all of the matrix material is removed from the column chamber.

4. The method of claim 1 wherein a first fluid is flowed into the column chamber during packing and a second fluid is flowed into the column chamber during unpacking, the second fluid being different from the first fluid.

5. A method of forming a packed column comprising: providing a column chamber, the column chamber having an inlet end and an outlet end, the outlet end having an actuator port and a flow port, the flow port alternately open or partially obstructed by a binary end of a rod placed in the actuator port wherein said binary end of said rod blocks the flow of a matrix material in a first position, permits the flow of said matrix material in a second position, and maintains contact with said fluid flow and allows the flow of a fluid in all positions; and flowing a mixture of a first fluid and a matrix material into the column chamber through the inlet end with said rod in said first position thereby packing the matrix material within the column chamber.

6. The method of claim 5 further comprising, after packing the matrix material in the column chamber, opening the flow port by a rotation of either of the rod or the column chamber with respect to the other and flowing a second fluid through the column chamber thereby unpacking the matrix material from the column chamber.

7. The method of claim 6 wherein the first fluid and the second fluid are the same.

8. A method for purifying a component of a sample comprising:

providing a column chamber, the column chamber having an inlet end and an outlet end, the outlet end having an actuator port and a flow port, the flow port alternately open or partially obstructed about a binary end of a rod placed in the actuator port wherein said binary end of said rod blocks the flow of a matrix material in a first position, permits the flow of said matrix material in a second position, and maintains contact with said fluid flow and allows the flow of a fluid in all positions;

flowing a first fluid and a matrix material into the column chamber through the inlet end and along a first flow path with said rod in said first position to form a packed column of the matrix material within the column chamber, the rod holding the matrix material and permitting flow of the first fluid therethrough, the matrix material being configured to selectively retain a component of the sample;

flowing the sample through the packed column for separating the component from the rest of the sample;

unobstructing the flow port by rotating said rod to said second position; and flowing a second fluid through the column to remove the matrix material from the column chamber.

9. The method of claim 8 wherein said sample is a chemical sample.

10. The method of claim 8 wherein the sample is a biological sample.

11. The method as recited in claim 10, wherein said biological sample has the component of a nucleic acid.

12. The method as recited in claim 10, wherein said biological sample has the component of a protein.

13. The method of claim 11 wherein the nucleic acid comprises at least one of DNA or RNA.

14. The method of claim 8 further comprising eluting the component from the packed column before removing the matrix material from the column chamber.

15. The method of claim 8 further comprising eluting the component from the matrix material after removing the matrix material from the column chamber.

16. The method of claim 8 further comprising recirculating at least some portions of the sample through the packed column prior to removing the matrix material from the column chamber.

17. A method for purifying a biological sample comprising:
providing a column chamber, the column chamber having an inlet end and an outlet end, the outlet end having an actuator port and a flow port, the flow port partially obstructed with a rod with a binary end wherein said binary end of said rod blocks the flow of a matrix material in a first position, permits the flow of said matrix material in a second position, and maintains contact with said fluid flow and allows the flow of a fluid in all positions;
flowing a mixture of a first fluid and a matrix material into the column chamber with said rod in said first position to form a packed column of the matrix material within the column chamber, the matirix material being configured to selectively retain a biological sample;
flowing a sample containing the biological sample through the packed column to separate the biological sample from other components of the sample; rotating said rod to said second position; and flowing a second fluid through the column chamber to remove the matrix material from the column chamber.

\* \* \* \* \*